(12) United States Patent
Van der Saag et al.

(10) Patent No.: US 11,141,420 B2
(45) Date of Patent: Oct. 12, 2021

(54) FLAVANONES FOR USE IN TREATING VISCERAL HYPERSENSITIVITY

(71) Applicant: BioActor BV, Maastricht (NL)

(72) Inventors: Antonie Johannes Van der Saag, Maastricht (NL); Bouke Salden, Maastricht (NL); Sam Possemiers, Maastricht (NL); Yala Stevens, Maastricht (NL)

(73) Assignee: BioActor BV, Maastricht (NL)

( * ) Notice: Subject to any disclaimer, the term of this patent is extended or adjusted under 35 U.S.C. 154(b) by 0 days.

(21) Appl. No.: 16/487,695

(22) PCT Filed: Feb. 23, 2018

(86) PCT No.: PCT/EP2018/054543
§ 371 (c)(1),
(2) Date: Aug. 21, 2019

(87) PCT Pub. No.: WO2018/154064
PCT Pub. Date: Aug. 30, 2018

(65) Prior Publication Data
US 2020/0230165 A1    Jul. 23, 2020

(30) Foreign Application Priority Data

Feb. 24, 2017  (EP) .................................. 17157905

(51) Int. Cl.
*A61K 31/70*   (2006.01)
*A01N 43/04*   (2006.01)
*A61K 31/7048* (2006.01)
*A61P 1/00*    (2006.01)

(52) U.S. Cl.
CPC .......... *A61K 31/7048* (2013.01); *A61P 1/00* (2018.01)

(58) Field of Classification Search
None
See application file for complete search history.

(56) References Cited

U.S. PATENT DOCUMENTS

| 2002/0037855 A1 | 3/2002 | Stanislaus |
| 2003/0078231 A1 | 4/2003 | Wilburn |

FOREIGN PATENT DOCUMENTS

| CN | 101474275 A | 7/2009 |
| CN | 101623366 A | 1/2010 |
| CN | 102416062 A | 4/2012 |
| EP | 0956867 A1 | 5/1998 |
| WO | 1998047534 | 10/1998 |
| WO | 2001015553 A1 | 3/2001 |
| WO | 2001026467 A1 | 4/2001 |
| WO | 2005094864 A2 | 10/2005 |
| WO | 2015006863 A1 | 1/2015 |

OTHER PUBLICATIONS

Wang et al. Herbal prescription Chang'an II repairs intestinal mucosal barrier in rats with post-inflammation irritable bowel syndrome . Acta Pharmacol Sin 36, 708-715 (2015). https://doi.org/10.1038/aps.2014.170.*
Collins et al. European Journal of Pharmacology (2011), vol. 668, pp. 271-277.*
McGonigle et al. Biochemical Pharmacology (2014), vol. 87, pp. 162-171.*
Kanaze et al. European Journal of Clinical Nutrition (2007), vol. 61, pp. 472-477.*
Sundin, Johanna, et al. "Cytokine response after stimulation with key commensal bacteria differ in post-infectious irritable bowel syndrome (PI-IBS) patients compared to healthy controls." PLoS One 10.9 (2015): e0134836.*
Chen, et al., "Development of determination of four analytes of Zhi-Shao-San decoction using LC-MS/MS and its application to comparative pharmacokinetics in normal and irritable bowel syndrome rat plasma: Determination of four analytes of Zhi-Shao-San decoction using LC-MS/MS", Biomedical Chromatography, vol. 28, No. 10, Mar. 28, 2014, pp. 1384-1392, XP055395024.
Brand, et al., "Stereoselective Conjugation, Transport and Bioactivity of S - nd R -Hesperetin Enantiomers in Vitro", Journal of Agricultural and Food Chemistry, vol. 58, No. 10, May 26, 2010, pp. 6119-6125, XP055395117.
Li, et al., "Comparative Pharmacokinetics of Naringin in Rat after Oral Administration of Chaihu-Shu-Gan-San Aqueous Extract and Naringin Alone", Metabolites, vol. 3, No. 4, Sep. 30, 2013, pp. 867-880, XP055395040.
Burak, et al., "Chronic pelvic pain associated with pelvic congestion syndrome and the benefit of Daflon 500 mg: A review", Phlebolymphology 2009 Servier International FRA, vol. 16, No. 3, 2009, pp. 290-294, XP002772742.
Kawaguchi, et al., "Colony Stimulating Factor-Inducing Activity of Hesperidin", Planta Med. 65, Letters, pp. 365-366, 1999.

(Continued)

*Primary Examiner* — Patrick T Lewis
(74) *Attorney, Agent, or Firm* — Dinsmore & Shohl LLP (57) ABSTRACT

The present invention relates to compounds of formula (I), such as hesperitin-7-rutinoside 2S, for use in the treatment of visceral hypersensitivity. Compounds and compositions of the invention are particularly useful in the treatment of visceral hypersensitivity in a subject having irritable bowel syndrome or age-associated low grade systemic inflammation of the gut, but lacking spasmodic intestinal contractions.

5 Claims, 3 Drawing Sheets

(56) References Cited

OTHER PUBLICATIONS

Unno, et al., "Hesperetin Modifies the Composition of Fecal Microbiota and Increases Cecal Levels of Short-Chain Fatty Acids in Rats", Journal of Agricultural and Food Chemistry, vol. 63, No. 36, Sep. 16, 2015, pp. 7952-7957, XP055395015.
International Search Report dated Apr. 12, 2018 in reference to co-pending European Patent Application No. PCT/EP2018/054543 filed Feb. 23, 2018.
Database WPI, Thompson Scientific, XP002772740, Jan. 13, 2010.
Database WPI, Thompson Scientific, XP002772741, Jul. 8, 2009.
Database WPI, Thompson Scientific, XP002882743, Apr. 18, 2012.
European Patent Office Search Report in reference to co-pending European Patent Application No. EP 17157905.5-1453 filed Aug. 14, 2017.

\* cited by examiner

FLAVANONES FOR USE IN TREATING VISCERAL HYPERSENSITIVITY

FIELD OF THE INVENTION

The present invention relates to compounds of formula I, such as hesperitin-7-rutinoside 2S, for use in the treatment of visceral hypersensitivity. Compounds and compositions of the invention are particularly useful in the treatment of visceral hypersensitivity in a subject having irritable bowel syndrome or age-associated low grade systemic inflammation of the gut, but lacking spasmodic intestinal contractions.

BACKGROUND TO THE INVENTION

Abdominal indefinite complaint or abdominal discomfort is a common problem in our daily lives. Abdominal discomfort is often caused by functional gastrointestinal disorders. Functional gastrointestinal disorders are characterized by chronic or recurrent gastrointestinal symptoms which are not explained by any organic, i.e. structural or biochemical, abnormality. In general, functional disorders should be distinguished from morphological or organic disorders in which the organ structures have been abnormally changed, for example in patients with inflammatory bowel disease (IBD).

A typical example of a functional gastrointestinal disorder is irritable bowel syndrome (IBS). IBS is an archetype disorder of functional gastrointestinal disorders with no underlying organic abnormality. IBS patients report continued lower gastrointestinal symptoms such as abnormal bowel movement, abdominal pain, abdominal bloating and abdominal discomfort, as well as upper gastrointestinal symptoms such as epigastric pain, hypochondriac pain, nausea, anorexia, vomiting, and heartburn.

Irritable bowel syndrome is thought to be a multifactorial disorder, symptoms are partially explained by inflammation, infection, gut motility, changed microflora, enhanced visceral sensitivity, brain-gut axis disturbances, increased intestinal permeability, and more, but no single mechanism can explain all IBS cases. Further, some patient with IBS also have spasmodic intestinal contractions, whereas other IBS patients lack these spasmodic intestinal contractions.

At present, visceral hypersensitivity (VHS) is considered as an important mechanism influencing the intensity of IBS, and is observed in 30-60% of all IBS patients. Some of these IBS patients suffering from visceral hypersensitivity will have intestinal spasmodic contractions, whereas others won't. VHS refers to an increased sensitivity to peripheral stimuli (mechanical, thermal, chemical and other) and is manifested through the development of pain, motor and/or secretory disturbances in response to a sub-threshold stimulus. Visceral hyperalgesia (the phenomenon whereby usually non-painful stimuli are appreciated as being painful) is one manifestation of VHS. VHS results from dysregulation of the bidirectional communication between the gut with its enteric nervous system and the brain, the gut-brain axis (GBA), which can be modulated by various psychosocial and environmental factors. Patients with IBS are often treated by medication that targets individual symptoms, resulting in limited treatment efficacy and the absence of a universal drug that fits all. In addition, there are only very few compositions known for the treatment of VHS in IBS patients.

VHS is also present in aging subjects, characterised by a state of chronic low grade systemic inflammation. The cause of this condition probably resides in age-associated microbial dysbiosis There is thus a continuing need for identifying novel options for the treatment of visceral hypersensitivity. In addition, active agents against VHS are generally synthetically created drugs. In view of the current patient's or consumer's focus on natural products and their aversion for synthetically created drugs, the identification of naturally-derived products for the treatment of VHS would be especially beneficial. Therefore, there is a continuing need for naturally-derived products for use in the treatment of VHS with IBS patients or an ageing population with microbial dysbiosis and systemic low grade inflammation.

SUMMARY OF THE INVENTION

It has surprisingly been found that the compounds such as hesperidin, its aglycone form hesperitin and close analogues can be used to treat visceral hypersensitivity in different subjects. In addition, improvements are observed when a flavanone of the hesperidin-like group is combined with naringin. Although not required, both products can be obtained easily from natural products, such as citrus fruits.

Hesperidin (also referred to herein as hesperitin-7-rutinoside) is a flavanone, a subclass of the flavonoids that is most abundant in the fruit of immature citrus fruits and in the peels of mature citrus fruits, and exhibits a wide range of physiological activity. Hesperidin is known to have vasodilative, hypotensive, anti-oxidative, anti-inflammatory, carcinostatic and prebiotic activities (e.g. EP0956867, WO199847534, WO200115553, US2002037855, US2003078231, etc.). Hesperidin is metabolized to its aglycone hesperitin by the gut microbiota, resulting in an increased bioavailability.

Naringin is a flavanone, a subclass of the flavonoids found in grapes and citrus fruits. Naringin is known to possess numerous biological properties such as antioxidant, anti-inflammatory, anti-apoptotic and anti-carcinogenic activities (e.g. WO200126467, US2002037855, WO05094864A2, etc.). Naringin is metabolized to its aglycone naringenin by the gut microbiota, resulting in an increased bioavailability.

Some particular health benefits attributed to citrus consumption have been correlated with the presence of some specific flavonoids. Flavonoids are polyphenolic compounds with diverse beneficial biochemical effects, including anti-oxidative, and anti-inflammatory activities that can modulate immune responses. Furthermore, some particular flavonoids can affect the microbiota composition and activity.

Therefore, in a first aspect, the invention provides the use of a compound of formula I wherein

R$_1$ is hydrogen or a saccharide consisting of 1 to 5 monosaccharide units; and

- - - represents a single or double bond;

for use in the treatment of visceral hypersensitivity; in particular for use in the treatment of visceral hypersensitivity in patients suffering from IBS but lacking spasmodic intestinal contractions and in elderly subjects with microbial dysbiosis and systemic low grade inflammation.

Hesperidin (also referred to herein as hesperitin-7-rutinoside) is a flavonoid, specifically a flavanone, which is commonly found in several plants, including citrus fruits (e.g. oranges, grapefruit) and roots from valerian species. Here, the compounds described herein for use in the invention may originate from any plant and may refer to any of the following: the native glycoside hesperidin, as well as partially deglycosylated forms, the aglycon form hesperitin, and farther metabolized derivatives that can result from bacterial digestion, intestinal uptake, and hepatic metabolism. They may further comprises any chemically or enzymatically derived derivative of any of the foregoing molecules.

In a second aspect, the invention provides the use of a compound as indicated above, wherein said compound is of formula Ia wherein R$_1$ is as defined above.

In another embodiment, R$_1$ in the compound of the invention, is hydrogen or a saccharide consisting of 1 to 5 rhamnose and/or glucose units.

In another embodiment, R$_1$ in the compound of the invention, is rhamnoglucosyl.

The inventors also observed a synergistic effect when compounds of formula I are combined with naringin or naringenin. Therefore, in another embodiment, the present invention provides a combination of (a) a compound of the invention, and (b) naringin or naringenin, for use in the treatment of visceral hypersensitivity. In a further embodiment, the present invention provides a composition comprising such a combination. In another particular embodiment, said naringin or naringenin is present in the composition in an amount of 1:10 to 1:35 in comparison to the weight of the compound of Formula I (or subformulae). In a further preferred embodiment, the weight of naringin or naringenin is about 3% to 7% of the weight of the compound of the invention, in particular about 5%.

Said composition is preferably an oral composition in the form of a liquid, solution, tablet, lozenge, dissolvable film, suspension, dietary gel, capsule, chewable or syrup.

In a particular embodiment, said composition for use is enantiomerically enriched for formula II wherein R$_1$ and - - - are as defined herein.

In a further embodiment, the present invention provides the use (supra) of a composition according to the invention, wherein said composition is enantiomerically enriched for formula IIa wherein R$_1$ is as defined herein.

In a further embodiment, the compound of formula I, Ia, II, or IIa is present in an amount of 50 mg to 1500 mg per unit dosage of said composition. If naringin or naringenin are present, they are preferably present in an amount of 2.5 mg to 150 mg per unit dosage of said composition; in particular in an amount of 5 mg to 100 mg, more in particular in an amount of 15 mg to 50 mg. Preferably, the compositions of the invention are administered once daily. Therefore, in a preferred embodiment, the compositions of the invention are administered in a daily dosage comprising the amounts mentioned herein as unit dosages.

In a further embodiment, the present invention provides the compounds, the combinations or the compositions described herein for use in the treatment of visceral hypersensitivity in a subject having irritable bowel syndrome but lacking spasmodic intestinal contractions.

In another embodiment, the present invention provides the compounds, combinations and compositions of the invention for use in the treatment of pain in a subject having irritable bowel syndrome.

In yet another embodiment, the present invention provides the compounds, combinations and compositions of the invention for use in the treatment of VHS in an elderly subject having chronic low grade systemic inflammation but lacking spasmodic intestinal contractions.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the inven-

DETAILED DESCRIPTION OF THE INVENTION

As described herein before, in a first aspect, the invention provides the use of a compound of formula I wherein
$R_1$ is hydrogen or a saccharide consisting of 1 to 5 monosaccharide units; and
--- represents a single or double bond;
for use in the treatment of visceral hypersensitivity; in particular for use in the treatment of visceral hypersensitivity in patients suffering from IBS but lacking spasmodic intestinal contractions and in elderly subjects with microbial dysbiosis and systemic low grade inflammation.

The term "visceral hypersensitivity" (VHS) as used herein refers to an increased sensitivity to peripheral stimuli (mechanical, thermal, chemical and other) and is manifested through the development of pain, motor and/or secretory disturbances in response to a sub-threshold stimulus.

In a second aspect, the invention provides the use of a compound as indicated above, wherein said compound is of formula Ia wherein $R_1$ is as defined herein.

In a certain embodiment, R1 as present in the compounds described herein, is hydrogen or a saccharide consisting of 1 to 5 rhamnose and/or glucose units; in particular 1 to 3; more in particular 1 or 2 rhamnose and/or glucose units. In a particular embodiment, R1 is rhamnoglucosyl; more in particular said compound is hesperidin. In another particular embodiment, R1 is hydrogen; more in particular said compound is hesperitin. In another particular embodiment, R1 is glucosyl; more in particular said compound is hesperitin 7-glucoside, e.g. as described in Nielsen et al. (J Nutr 2006, 136:404-408). In yet another particular embodiment, said compound is glucosyl hesperidin, e.g. as described in Yamada et al. (Biosci Biotechnol Biochem 2006, 70:1386-94).

In another particular embodiment, the compounds for use of the present invention are selected from hesperidin, diosmin, and neohesperidin, or their aglycon forms hesperitin neohesperitin, and diosmetin. In a further embodiment, said compound is hesperidin or hesperitin, in particular hesperidin.

In a certain production method, hesperidin is extracted from the whole fruit of sweet oranges (immature dried fruit). An extracted liquid is retrieved following alkaline extraction. This liquid is treated with sulfuric acid ($H_2SO_4$) to obtain hesperitin-7-rutinoside 2S, which is eventually treated with a mixture of $H_2SO_4$ and sodium hydroxide (NaOH) to obtain the finished hesperitin-7-rutinoside 2S.

In another embodiment, the mentioned compounds, in particular hesperidin is combined with naringin or naringenin, for use in the treatment of visceral hypersensitivity.

A further embodiment provides the compound (supra), optionally co-extracted or combined with naringin or naringenin in a composition for use in the treatment of visceral hypersensitivity.

Studies have shown good bioavailability of hesperidin and analogues described herein as well as naringin or naringenin when administered orally. It is therefore an object of the invention to provide compounds and compositions comprising the compounds described herein that can be orally administered, for use in the treatment of visceral hypersensitivity. Preferred compositions for oral administration include but are not limited to:

Sub-lingual films, tablets, or lozenges (tablets that slowly dissolve in the mouth) that ensure uptake of the compounds described herein through sublingual and/or buccal mucosa, bypassing the intestinal microflora and hepatic circulation.

Composition of citrus fruit or peel extract comprising the compounds described herein, which is active when taken orally in typical dosage forms like capsules, beverages, and food products.

In a particular embodiment, the composition is an oral composition in the form of a liquid, solution, tablet, lozenge, dissolvable film, suspension, dietary gel, capsule, chewable or syrup.

In a preferred embodiment, a composition of the invention comprises an isolated compound of the invention or the composition has been enriched for the compound of the invention. In another particular embodiment, the composition of the invention comprises a compound of the invention and a bulking agent. The bulking agent is preferably of natural origin. Examples of bulking agents suitable for the method of administration are known to the person skilled in the art. Preferably, the bulking agent is a saccharide, including mono-, oligo- and polysaccharides; in particular a sugar or natural gum. In a further embodiment, the bulking agent is selected from the below list described for pharmaceutical carriers.

The invention relates to a composition comprising a compound of the invention, wherein the composition is a pharmaceutical composition further comprising a pharmaceutically acceptable carrier. Examples of pharmaceutical carriers are known to the person skilled in the art and include but are not limited to D-mannitol, sorbitol, sucrose, galactose, cellulose, other sugars, other saccharides, other oligosaccharides and/or polysaccharides, gelatin, guar gum, Arabic gum, agar agar, xanthan gum, locust bean gum, starch, starch fragments, dextrins, British gum and any mixture thereof. Preferably, the pharmaceutical acceptable carrier is of natural origin.

In another aspect, the invention relates to a composition comprising a compound of the invention, wherein the composition is in a form suitable for sublingual and/or buccal administration, wherein the composition is in the form of a liquid solution, (disintegrating) tablet, lozenge, dissolvable film, suspension, (dietary) gel, capsule, chewable or syrup.

'Tablets' refer to a dosage form comprising a mixture of one or more active substances including inner filler substances such as, desintegrants, binding agents, lubricants, glidants, antiadherents, flavors, coloring agents etc.

'Disintegrating tablets' are tablets with a specific composition that quickly disintegrates when getting in contact with saliva in the mouth or with water. These tablets may have the same composition as regular tablets, however, added with components optimized for disintegration time, e.g. by adding desintegrants.

'Capsules' consist of a thin layer outer wall, made from a substance that dissolves in the stomach and/or intestinal fluid, e.g. gelatin, agar etc. Capsules can be filled with the active substance as a dry powder, or as a fluid consisting of different solutions etc. that contain the active ingredient.

'Syrups' are sweetened, flavored, viscose solution that contains a certain concentration of the active substance, which can be diluted into a food or drink.

'Dietary gels' refers to highly viscous aqueous solutions of active substances that may be added with flavoring and coloring agents in the presence of a gelling agent such as gelatin, agar, acacia gums and others. This mixture of components is presented as a slowly flowing or semi-solid substance.

'Lozenges' refer to hardened mixtures of the active ingredient and additional substances that slowly dissolve when getting into contact with the saliva in the mouth, elaborating a prolonged exposure of the active substance with the buccal mucosa. Lozenges often contain flavoring and sweeteners to increase palatability.

The active ingredient can be applied in any form, according to the various embodiments of the present invention. For instance, the dosage form of the active ingredient may be provided as, e.g., a powder beverage mix, beverage syrup, a liquid beverage, a ready-to-eat bar or drink product, a capsule, a liquid capsule, a tablet, a caplet, a lozenge, a chewable tablet, dissolvable film, a dietary gel, or syrup.

Therefore, in one embodiment, the invention relates to a composition comprising a compound of the invention, wherein the composition is a food, beverage, or supplement composition for a food composition, for example a nutrition bar or a ready to drink powdered beverage.

In one embodiment, the invention relates to a composition comprising a compound of the invention, wherein the composition is a food, beverage, or supplement composition for a food or a beverage, for example a nutrition bar or drinks, used as medical food.

In another embodiment, the invention refers to a composition comprising a compound of the invention, wherein the composition is in a form suitable for sublingual and/or buccal administration, wherein the composition is a food, beverage, or a supplement composition for a food or a beverage, for example a nutrition bar.

Hesperitin-7-rutinoside after extraction without enantiomeric enrichment, is a mixture of an R- and S-anantiomers, the R:S molar ratio of which is between 1:1 and 1:5, depending on its source. A mixture of R- and S-enantiomers which has a molar ratio of 1; 1 is also known as a racemic mixture. Hesperidin may refer to racemic hesperidin, preferably to enantiomerically enriched hesperidin, more preferably hesperidin which is enantiomerically enriched in (2S)-hesperidin. With 'enantiomerically enriched' is meant that the hesperidin has an excess of one enantiomer over the other. Enantiomeric enrichment can be achieved amongst other methods known by a person skilled in the art by selection of the botanic source of hesperidin, and/or stereochemical separation techniques, such as capillary electrophoresis (CE). It has been observed that the compounds of the invention have an increased bioavailability when enantiomerically enriched.

Therefore, in a particular embodiment, said composition for use is enantiomerically enriched for formula II wherein $R_1$ and --- are as defined herein.

In another particular embodiment, the present invention provides a composition according to the invention, wherein said composition is enantiomerically enriched for formula IIa wherein $R_1$ is as defined herein.

Dosages

The optimal dose of the compounds of the invention (formula I, Ia, II or IIa) for humans, preferably human adults, can be derived using the FDA recommendations for translating to the human equivalent dose (HED) from animal studies. This recommendation translates the dosages used for animal studies to dosages per day for the general population (i.e. average human adults).

Preferably, the compound of the invention is administered (to a human adult) once daily in an amount of approximately 50-1500 mg. The ingredient is preferably administered during the morning.

In another particular embodiment, the present invention provides the daily administration of the compound of formula I, Ia, II or IIa in an amount of 50 mg to 1500 mg; in particular from 100 mg to 1000 mg; more in particular from 150 mg to 750 mg. In yet another particular embodiment from 400 mg to 600 mg; in particular from 450 mg to 550 mg. In another embodiment from 250 mg to 1000 mg. In a preferred embodiment, the invention provides a composition in unit dosages, wherein a compound of formula I, Ia, II or IIa is present per unit dosage in an amount as described above for daily administration.

In a further embodiment, the compound of formula I, Ia, II, or IIa is present in an amount of 50 mg to 1500 mg per unit dosage of said composition. Furthermore, naringin or naringenin are present in an amount of 2.5 mg to 150 mg per unit dosage of said composition.

The subject to be treated is preferably a mammal, in particular a human. In a particular embodiment, the subject has irritable bowel syndrome but lacks spasmodic intestinal contractions.

In another particular embodiment, the present invention provides the compounds, combinations and compositions disclosed herein for the treatment of pain; in particular for the treatment of pain in a subject having IBS; more in particular for the treatment of abdominal pain in a subject having IBS.

The compound, the combination or the composition indicated herein, in particular hesperidin in combination with naringin or naringenin are also useful to:
- improve the intestinal function, by modulating the intestinal microbiota composition, more in specific promote the growth of butyrate-producing bacteria, such as Clostridium cluster XIVa, more in particular Escherichia rectale or Clostridium coccoides.
- Enhance the intestinal barrier function
- Lower fecal calprotectin
- Increase the production of lactate and lower the pH in the intestinal lumen
- Improve IBS symptoms, more specific IBS lacking spasmodic intestinal contractions.
- Lower the pathogen pressure in the gut
- Improve the gut barrier function and the immune system Example 1

Methods

To study the effect of the composition of the invention on the gut microbiota, a Simulator of the Human Intestinal Microbial Ecosystem (SHIME) was used. Two identical units of the SHIME were operated in parallel (TWIN-SHIME) according to Molly et al (Microbial Ecology in Health and Disease 1994, 7:191-200). 500 mg orange fruit extract comprising 380 mg Hesperidin (enriched for the 2S form) or a control was administered in the simulator each day for 3 weeks. The effect of the composition of the invention was studied by monitoring short chain fatty acids (SOFA) and lactate production, additionally qPCR analysis was performed to determine the gut microbial composition.

Results

Figure 1:
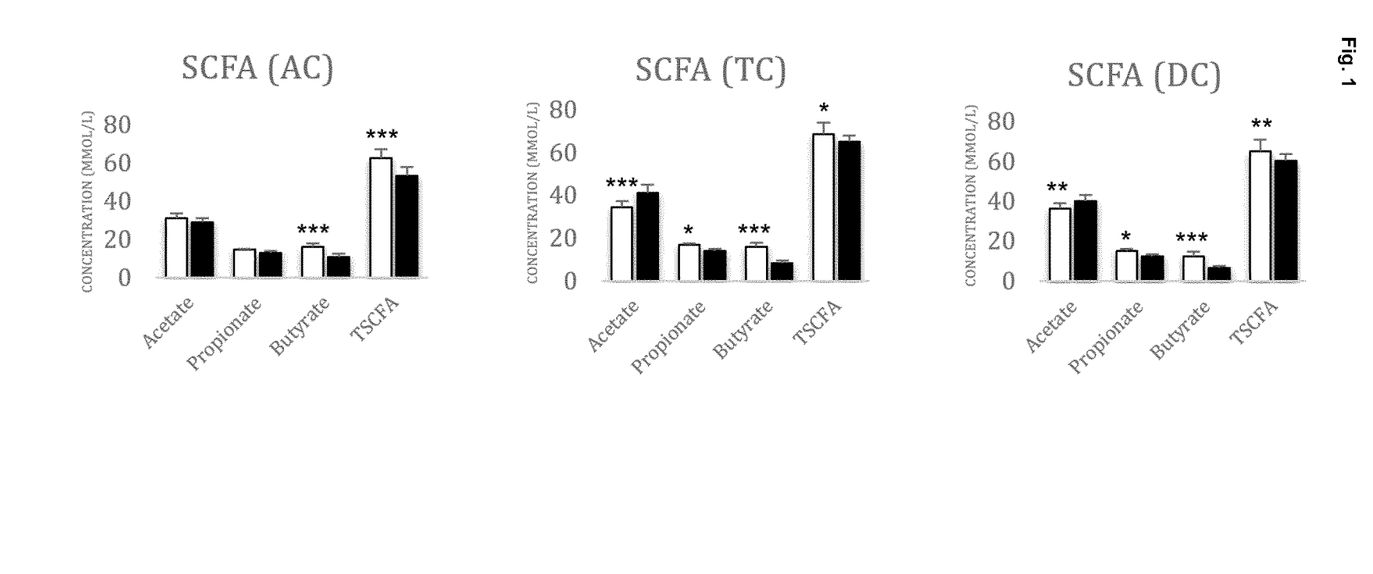
FIG. 1: SCFA concentrations in the different colon compartments. White bars: treatment group, black bars: control.

Daily in vitro digestion of the composition of the invention in the SHIME showed an increase in butyrate and total SOFA (TSCFA) in the colon. SOFA concentrations during the SHIME experiment are presented in FIG. 1 (white bars: treatment with composition of the invention; black bars: administration of control composition).

Figure 2:
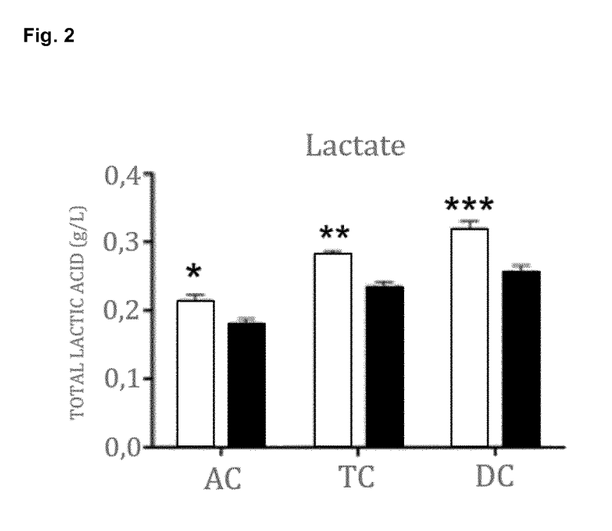
FIG. 2: Lactate production during the SHIME experiment. White bars: treatment group, black bars: control.

During the three week treatment period, lactate concentrations showed a stronger increase with the composition of the invention compared to the control SHIME run. This is shown in FIG. 2 (white bars: treatment with composition of the invention; black bars: administration of control composition).

Figure 3:
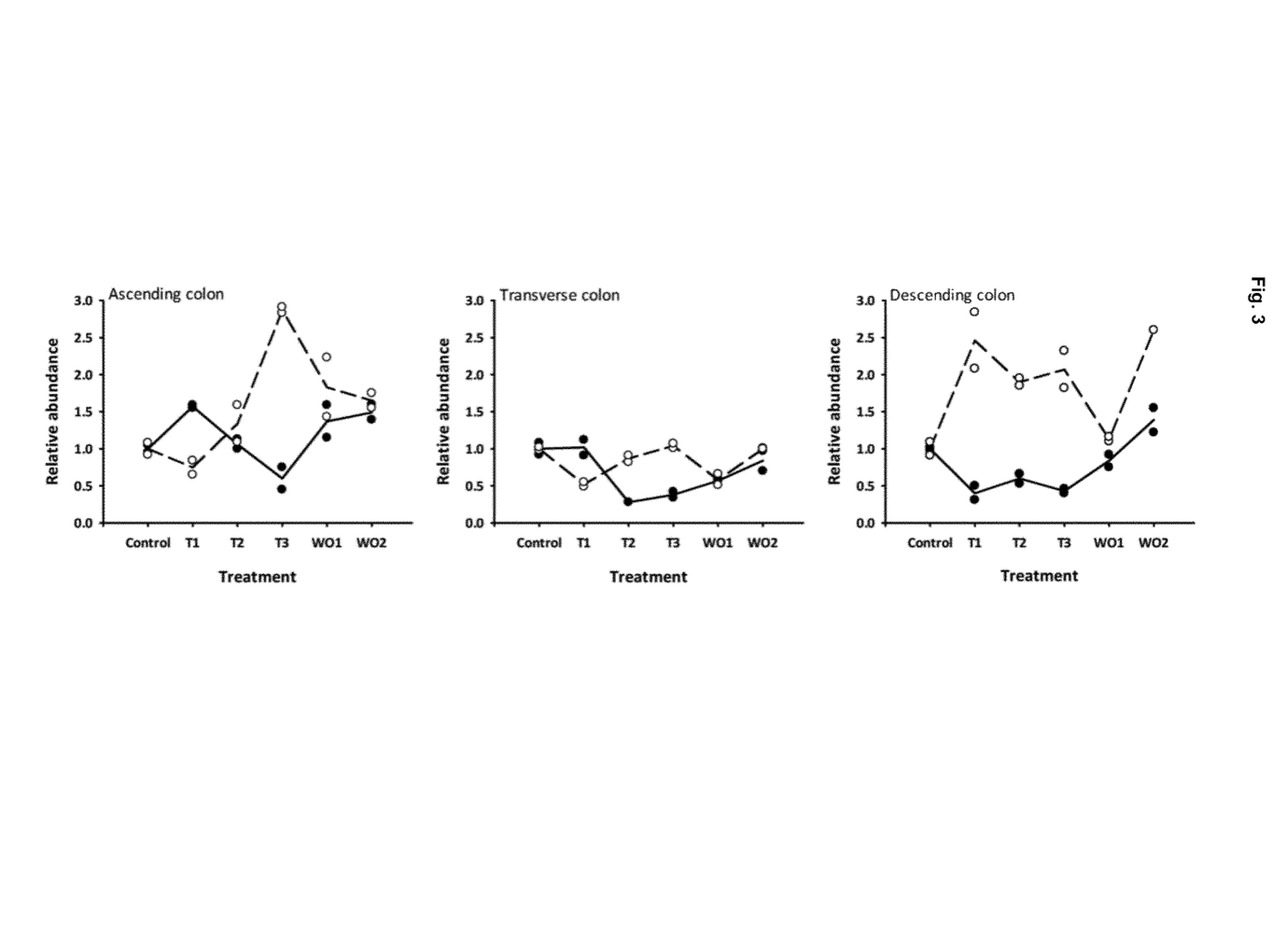
FIG. 3: Relative abundance of *Escherichia rectale/Clostridium coccoides* in the different colon compartments. White bullets: treatment group, black bullets: control.

As shown in FIG. 3, after one week of treatment with the composition of the invention, up to 2.5 fold butyrate producing bacteria growth was observed in the descending colon (DC). Major increases were observed for Clostridium cluster XIVa, in particular E. rectale and C. coccoides, This effect persisted during the wash out phase. These data are shown in FIG. 3 (white points: treatment with composition of the invention; black points: administration of control composition).

Example 2

Methods

Subjects in an age bracket between 65 and 75 years old with chronic low grade systemic inflammation of the gut were randomly allocated to the following two treatment groups.

Group 1: Test substance (Citrus Sinensis extract) containing 75% of Hesperidin 2S, 500 mg/day Group 2: Matching placebo (Cellulose), 500 mg/day Each group received oral test substance (capsules) or placebo (capsules) daily for 12 weeks. Test substance or placebo was taken each day just before breakfast. Measurement of fecal calprotectin and fecal short-chain fatty acids (SCFA) was performed at baseline and 12 weeks after initiation of the treatments.

Results

As shown in Table 1, the test substance of this invention was able to improve SCFA profiles and calprotectin levels in elderly subjects with chronic low grade systemic inflammation of the gut and age-associated microbioal dysbiosis.

TABLE 1

Effect of test substance on SCFA profiles and fecal calprotectin in subjects at risk for metabolic syndrome

| | Test substance | | Placebo | | |
| --- | --- | --- | --- | --- | --- |
| | Baseline | 12 weeks | Baseline | 12 weeks | P-value |
| Calprotectin (ng/mL) | 32.9 ± 7.8$^2$ | 42.5 ± 7.6 | 47.5 ± 8.7 | 37.1 ± 8.4 | 0.05 |
| Acetate/total SCFA ratio | 0.61 ± 0.01 | 0.62 ± 0.01 | 0.61 ± 0.01 | 0.60 ± 0.02 | 0.249 |
| Propionate/total SCFA ratio | 0.20 ± 0.01 | 0.20 ± 0.01 | 0.21 ± 0.01 | 0.20 ± 0.01 | 0.079 |
| Butyrate/total SCFA ratio | 0.19 ± 0.01 | 0.18 ± 0.01 | 0.18 ± 0.01 | 0.20 ± 0.01 | 0.812 |
| Butyrate/acetate ratio | 0.32 ± 0.02 | 0.29 ± 0.02 | 0.31 ± 0.03 | 0.35 ± 0.02 | 0.031 |

Example 3

Methods

Subjects were recruited from 2 different patient populations.

Population 1: 30 patients with quiescent ulcerative colitis, calprotectin levels 50-150 µg/g feces and age 18-70 years.

Population 2:

The second group consisted of: 30 patients with irritable bowel syndrome, calprotectin levels 15-150 µg/g feces and age 18-70 years.

The subjects were randomly allocated to the following two treatment groups.

Group 1: Test substance: 500 mg of citrus extract comprising 375 mg hesperidine and 25 mg of naringin per day Group 2: Matching placebo: 500 mg maltodextrin per day Each group received oral test substance (capsules) or placebo (capsules) daily for 8 weeks. Test substance or placebo was taken each day just before breakfast. Measurements of fecal calprotectin, fecal short-chain fatty acids (SOFA), microbiota composition, systemic immune response and disease symptoms were performed at baseline and 8 weeks after initiation of the treatments.

Results

Results showed a decrease in fecal calprotectin, a SOFA shift towards butyrate, an increase in *Clostridium* cluster XIVa, an improved gut barrier function, reduction of gut leakiness, a lowered immune response and improvements in IBS symptoms, including a decrease of visceral pain.

Example 4

Methods

IBS patients without spasmodic intestinal contractions (included using the Bristol stool chart and the GSRS-IBS questionnaire) were randomly allocated to the following two treatment groups.

Group 1: Test substance as in example 3

Group 2: Matching placebo as in example 3

Each group received oral test substance (capsules) or placebo (capsules) daily for 8 weeks. Test substance or placebo was taken each day just before breakfast. Measurements of disease symptoms were performed using the Gastrointestinal Symptom Rating Scale (GSRS)-IBS questionnaire and the symptoms diary. The GSRS questionnaire was filled in at baseline, after 4 weeks and after 8 weeks of supplementation. The symptoms diary was filled in daily for duration of 9 weeks (starting one week prior to supplementation until the end of the study).

Results

Results showed improvements in visceral hypersensitivity in subjects treated with the composition of the invention vs. placebo.

The invention claimed is:

1. A method for treating microbial dysbiosis and chronic low grade systemic inflammation in an elderly subject with microbial dysbiosis and chronic low grade systemic inflammation, the method comprising administering to the elderly subject a pharmaceutical composition comprising 50 mg to 1500 mg hesperidin per unit dosage.

2. The method of claim 1, further comprising administering naringin or naringenin to the elderly subject.

3. The method of claim 1, wherein the hesperidin is administered to the elderly subject in a pharmaceutical composition.

4. The method of claim 3, wherein the pharmaceutical composition is an oral pharmaceutical composition in the form of a liquid, powdered beverage, solution, tablet, lozenge, dissolvable film, suspension, dietary gel, capsule, chewable, or syrup.

5. The method of claim 3, further comprising administering 2.5 mg to 150 mg per unit dosage of naringin or naringenin to the elderly subject.

* * * * *

UNITED STATES PATENT AND TRADEMARK OFFICE
CERTIFICATE OF CORRECTION

PATENT NO. : 11,141,420 B2
APPLICATION NO. : 16/487695
DATED : October 12, 2021
INVENTOR(S) : Antonie Johannes Van der Saag et al.

It is certified that error appears in the above-identified patent and that said Letters Patent is hereby corrected as shown below:

On the Title Page

Column 2, item [56], Line 1, delete "Wang et al." and insert --Wang et al.,--, therefor.

Column 2, item [56], Line 2, delete "Collins et al." and insert --Collins et al.,--, therefor.

Column 2, item [56], Line 3, delete "McGonigle et al." and insert --McGonigle et al.,--, therefor.

Column 2, item [56], Line 4, delete "Kanaze et al." and insert --Kanaze et al.,--, therefor.

Column 2, item [56], Line 5, delete "Sundin, Johanna, et al." and insert --Johann Sundin et al.,--, therefor.

Column 2, item [56], Line 6, delete "Chen, et al.," and insert --Chen et al.,--, therefor.

Column 2, item [56], Line 7, delete "Brand, et al.," and insert --Brand et al.,--, therefor.

Column 2, item [56], Line 7, delete "nd" and insert --and--, therefor.

Column 2, item [56], Line 8, delete "Li, et al.," and insert --Li et al.,--, therefor.

Column 2, item [56], Line 10, delete "Kawaguchi, et al.," and insert --Kawaguchi et al.,--, therefor.

Page 2, Column 1, item [56], Line 1, delete "Unno, et al.," and insert --Unno et al.,--, therefor.

In the Specification

Column 10, Line 2, delete "(SOFA)" and insert --(SCFA)--, therefor.

Column 10, Line 7, after "total", delete "SOFA" and insert --SCFA--, therefor.

Signed and Sealed this
Eleventh Day of October, 2022

Katherine Kelly Vidal
*Director of the United States Patent and Trademark Office*

Column 10, Line 7, before "concentrations", delete "SOFA" and insert --SCFA--, therefor.

Column 11, Line 21, delete "(SOFA)" and insert --(SCFA)--, therefor.

Column 11, Line 25, delete "SOFA" and insert --SCFA--, therefor.